United States Patent
Paul et al.

(10) Patent No.: US 10,905,494 B2
(45) Date of Patent: Feb. 2, 2021

(54) FLEXIBLE CONDUCTIVE POLYMER BASED CONFORMABLE DEVICE AND METHOD TO CREATE LINEAR ENDOCARDIAL LESIONS

(75) Inventors: Saurav Paul, Minneapolis, MN (US); Riki Chou Thao, Brooklyn Park, MN (US)

(73) Assignee: ST. JUDE MEDICAL, ATRIAL FIBRILLATION DIVISION, INC, St. Paul, MN (US)

(*) Notice: Subject to any disclaimer, the term of this patent is extended or adjusted under 35 U.S.C. 154(b) by 618 days.

(21) Appl. No.: 13/340,127

(22) Filed: Dec. 29, 2011

(65) Prior Publication Data

US 2013/0172874 A1    Jul. 4, 2013

(51) Int. Cl.
| | | |
|---|---|---|
| A61B 18/14 | (2006.01) | |
| A61B 18/00 | (2006.01) | |
| A61B 17/00 | (2006.01) | |
| A61B 90/00 | (2016.01) | |

(52) U.S. Cl.
CPC ............. *A61B 18/1492* (2013.01); *A61B 2017/00039* (2013.01); *A61B 2017/00053* (2013.01); *A61B 2018/00357* (2013.01); *A61B 2018/00577* (2013.01); *A61B 2018/00875* (2013.01); *A61B 2018/1407* (2013.01); *A61B 2090/065* (2016.02)

(58) Field of Classification Search
CPC .................................................. A61B 18/1492
USPC ........................................................ 606/41
See application file for complete search history.

(56) References Cited

U.S. PATENT DOCUMENTS

| | | | |
|---|---|---|---|
| 5,800,482 A | * | 9/1998 | Pomeranz ........ A61B 17/00234 606/41 |
| 5,836,947 A | * | 11/1998 | Fleischman ........ A61B 18/1492 606/41 |
| 6,071,282 A | * | 6/2000 | Fleischman ........ A61B 18/1492 600/374 |
| 6,106,518 A | * | 8/2000 | Wittenberger ......... A61B 18/02 606/21 |
| 6,233,476 B1 | | 5/2001 | Strommer et al. |
| 6,291,568 B1 | | 9/2001 | Lussey |
| 6,332,880 B1 | * | 12/2001 | Yang ................ A61M 25/0043 604/528 |
| 6,495,069 B1 | | 12/2002 | Lussey et al. |
| 6,498,944 B1 | | 12/2002 | Ben-Haim et al. |
| 6,646,540 B1 | | 11/2003 | Lussey |
| 6,690,963 B2 | | 2/2004 | Ben-Haim et al. |
| 6,788,967 B2 | | 9/2004 | Ben-Haim et al. |
| 6,999,821 B2 | | 2/2006 | Jenney et al. |
| 7,197,354 B2 | | 3/2007 | Sobe |
| 7,263,397 B2 | | 8/2007 | Hauck et al. |

(Continued)

*Primary Examiner* — Rex R Holmes
*Assistant Examiner* — Jennifer L Ghand
(74) *Attorney, Agent, or Firm* — Dykema Gossett PLLC (57) ABSTRACT

An ablation device for creating linear lesions comprises a flexible support structure defining at least a partial curve; and an electrode disposed on the flexible support structure. The electrode comprises a pressure sensitive conductive composite that is configured for electrical communication with an electrical conductor and a flexible conductive outer covering that covers at least a portion of the pressure sensitive conductive composite. Electrical resistance of the pressure sensitive conductive composite varies inversely in proportion to pressure that is applied to the pressure sensitive conductive composite. Methods of creating linear lesions are also provided.

27 Claims, 7 Drawing Sheets

(56) References Cited

U.S. PATENT DOCUMENTS

| | | |
|---|---|---|
| 7,386,339 B2 | 6/2008 | Strommer et al. |
| 7,536,218 B2 | 5/2009 | Govari et al. |
| 7,789,877 B2 | 9/2010 | Vanney |
| 7,883,508 B2 | 2/2011 | Theo et al. |
| 7,955,326 B2 | 6/2011 | Paul et al. |
| 2003/0014051 A1* | 1/2003 | Woloszko .......... A61B 18/1477 606/46 |
| 2003/0078577 A1* | 4/2003 | Truckai et al. ................. 606/51 |
| 2003/0088244 A1* | 5/2003 | Swanson ................. A61L 31/10 606/41 |
| 2004/0215185 A1 | 10/2004 | Truckai et al. |
| 2005/0004440 A1* | 1/2005 | Vanney .............. A61B 18/1492 600/374 |
| 2006/0069388 A1* | 3/2006 | Truckai et al. ................. 606/45 |
| 2006/0084968 A1* | 4/2006 | Truckai et al. ................. 606/41 |
| 2006/0084969 A1* | 4/2006 | Truckai et al. ................. 606/41 |
| 2007/0066972 A1 | 3/2007 | Ormsby et al. |
| 2008/0161786 A1 | 7/2008 | Belhe et al. |
| 2008/0161789 A1* | 7/2008 | Thao et al. ...................... 606/34 |
| 2008/0161889 A1 | 7/2008 | Paul et al. |
| 2009/0158852 A1 | 6/2009 | Paul et al. |
| 2009/0163916 A1 | 6/2009 | Paul et al. |
| 2012/0059255 A1* | 3/2012 | Paul ....................... A61N 1/327 600/431 |

\* cited by examiner

FLEXIBLE CONDUCTIVE POLYMER BASED CONFORMABLE DEVICE AND METHOD TO CREATE LINEAR ENDOCARDIAL LESIONS

BACKGROUND OF THE INVENTION a. Field of the Invention

The instant invention relates to an ablation device for creating linear lesions. In particular, the instant invention relates to an ablation device and methods for creating linear lesions in which the ablation device has a flexible support structure defining at least a partial curve and an electrode comprising a pressure sensitive conductive composite and a flexible conductive outer covering.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, and/or microwave ablation. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue of a wide variety of cardiac anatomies across the entire length of the ablation electrode surface.

Current techniques for creating continuous linear lesions in endocardial applications include, for example, dragging a conventional catheter on the tissue, using an array electrode, or using pre-formed electrodes. These catheter designs require significant technical skill on the part of the surgeon in guiding and placing the catheter by sensitive steering mechanisms. Further, many of these devices comprise rigid electrodes that do not always allow the electrodes to conform to the highly varying anatomical topography of the endocardium tissue surface, especially when sharp gradients and undulations are present, such as at the ostium of the pulmonary vein in the left atrium and the isthmus of the right atrium between the inferior vena cava and the tricuspid valve. For example, in some instances, an arrhythmia may be caused by stray electrical signals moving along a pathway down the pulmonary veins and into the left atrium, and it may be desirable to produce a circumferential lesion at the ostium to one or more of the pulmonary veins or within one or more of the pulmonary veins to attempt to break or alter the flow of such stray electrical signals. Consequently, continuous linear lesions may be difficult to achieve. Additionally, with a rigid catheter, it can be difficult to maintain sufficient contact pressure until an adequate lesion has been formed. This problem is exacerbated on contoured or trabecular surfaces. If continuous and uniform contact between the electrode and the tissue cannot be properly maintained, any ablation lesions formed may not be adequate. For example and without limitation, any ablation lesions formed may be incomplete and/or spotty. Moreover, a lack of conformation of the electrode to the endocardium tissue surface can lead to maldistribution of irrigation fluid (if used), uncontrollable electric-field distribution, hot spots, and/or char formation.

BRIEF SUMMARY OF THE INVENTION

It is desirable to be able to provide an ablation device that improves the formation of uniform and continuous linear lesions, including transmural lesions, on smooth or contoured surfaces.

An ablation device for creating linear lesions comprises a flexible support structure defining at least a partial curve. The support structure can comprise a super elastic metal alloy material in accordance with an embodiment of the disclosure. For example and without limitation, the support structure can comprise a nickel-titanium alloy. The support structure can comprise a flat wire in accordance with an embodiment of the disclosure. The support structure can include a layer of insulating material extending over at least a portion of an outer surface of the support structure.

The ablation device further comprises an electrode disposed on the flexible support structure. The electrode comprises a pressure sensitive conductive composite that is configured for electrical communication with an electrical conductor, and a flexible conductive outer covering that covers at least a portion of the pressure sensitive conductive composite. The electrical resistance of the pressure sensitive conductive composite varies inversely in proportion to pressure that is applied to the pressure sensitive conductive composite. For example and without limitation, the pressure sensitive conductive composite has an electrical resistance greater than 100,000 ohms in a quiescent state in an embodiment of the disclosure. The pressure sensitive conductive composite has an electrical resistance greater than 1M ohms in a quiescent state in an embodiment of the disclosure. The pressure sensitive conductive composite has an electrical resistance greater than 10M ohms in a quiescent state. The electrical resistance of the pressure sensitive conductive composite is configured to fall below one ohm when a predefined amount of pressure is applied to the pressure sensitive conductive composite. For example and without limitation, the pressure sensitive conductive composite comprises a quantum tunneling composite.

The flexible conductive outer covering is in electrically conductive contact with the pressure sensitive conductive composite. The flexible conductive outer covering comprises polyacetylene, polypyrrole, polyanaline, or a combination thereof in accordance with some embodiments of the disclosure. The flexible conductive outer covering comprises a nonconductive polymer with electrically conductive particles dispersed therein in accordance with other embodiments of the disclosure. The nonconductive polymer can comprise silicone, and the electrically conductive particles can comprise gold, silver, platinum, iridium, titanium, tungsten, or a combination thereof. For example and without limitation, the flexible conductive outer covering can comprise a conductive silver fabric.

A method of creating linear lesions is also provided. The method can include the steps of forming a flexible, super elastic support structure defining at least a partial curve; inserting the support structure through at least a portion of a pressure sensitive conductive composite comprising a quantum tunneling composite, wherein electrical resistance of the quantum tunneling composite varies inversely in proportion to pressure that is applied to the quantum tunneling composite; and covering at least a portion of an outer surface of the pressure sensitive conductive composite with a flexible conductive outer covering to form an electrode. The electrical resistance of the quantum tunneling composite can be configured to fall below one ohm when a predefined amount of pressure is applied to the quantum tunneling composite. In accordance with an embodiment of the disclosure, the step of inserting the support structure through at least a portion of a pressure sensitive composite can comprise the substep of inserting the support structure through a plurality of pills comprising a quantum tunneling composite. The method can further include the steps of deploying the support structure; positioning the electrode in contact with tissue to be treated; coupling an RF energy supply to the electrode; and delivering RF energy to the tissue to be treated.

An ablation device for creating linear lesions in targeted tissue can comprise a super elastic support structure defining a loop; a layer of insulating material extending over at least a portion of an outer surface of the support structure; an electrode disposed on the support structure; and heat shrinkable tubing extending over at least a portion of the support structure and at least a portion of the electrode. The electrode can comprise a pressure sensitive conductive composite that is configured for electrical communication with an electrical conductor, wherein the pressure sensitive conductive composite comprises a quantum tunneling composite; and a flexible conductive outer covering that covers at least a portion of the pressure sensitive conductive composite and is in electrically conductive contact with the pressure sensitive conductive composite; and The foregoing and other aspects, features, details, utilities, and advantages of the present invention will be apparent from reading the following description and claims, and from reviewing the accompanying drawings.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal,"

"up," and "down" may be used herein with respect to the illustrated embodiments. However, surgical instruments may be used in many orientations and positions, and these terms are not intended to be limiting and absolute.

The instant disclosure generally relates to ablation devices. For purposes of this description, similar aspects among the various embodiments described herein will be referred to by similar reference numbers. As will be appreciated, however, the structure of the various aspects may be different among the various embodiments.

As generally shown in the embodiment illustrated in FIGS. 1A-1C and 2A-2C, ablation device 10, 110 comprises a support structure 12, 112 and an electrode 14, 114. While support structures 12, 112 may be different structurally (e.g., each may have a different loop length), support structures 12, 112 may be generally similar and the description below regarding support structure 12 may equally apply to support structure 112.

Support structure 12 may define a curve, such as a partial or complete curve or loop, at its distal end. Such a support structure 12 can be configured particularly for an ablation procedure at a pulmonary vein in or at the left atrium. In particular, the curved shape of the support structure 12 can facilitate formation of a continuous or nearly continuous lesion around the inside wall within one or more of the pulmonary veins or within the left atrium at the ostium to one or more of the pulmonary veins when ablation energy is transmitted to the target vein. The support structure 12 may define a first generally straight region 16 that is generally coaxially aligned with the distal end region of a catheter shaft or sheath 17 (see FIG. 1C). Following the generally straight region 16 is a generally curved region 18. The curved region 18 can form any closed or unclosed curved or generally arcuate shape, such as a partial or complete circle or ellipse.

The support structure 12 can comprise a generally flat wire in accordance with an embodiment of the disclosure. The support structure 12 can be flexible in accordance with an embodiment of the disclosure. In particular, the support structure 12 can be sufficiently flexible so as to be able to at least substantially conform to the targeted tissue of the endocardial or vascular wall. In particular, the support structure 12 can be sufficiently flexible so as to be bent and formed into various shapes to provide better contact to the tissue. For example and without limitation, the support structure 12 can be configured to be formed into a shape that substantially conforms to the targeted tissue of the endocardial or vascular (e.g., such as a pulmonary vein) wall during an ablation procedure. The support structure 12 can be sufficiently flexible so as to be configured to deform so as to be able to at least substantially conform to the targeted tissue of the endocardial or vascular wall.

The support structure 12 can be fabricated of a super elastic metal alloy material, such as nickel-titanium alloy in accordance with an embodiment of the disclosure. One such suitable nickel-titanium alloy is commonly referred to as "Nitinol." Generally, a suitable super elastic material for the support structure 12 is a shape memory alloy with a transformation temperature below that of the human body temperature. Alternatively, the shape memory alloy may also have a transformation temperature above that of the human body. If the shape memory alloy has a transformation temperature above that of the human body, an electric current can be applied to the shape memory alloy material to convert it into a super elastic state. When such a super elastic shape memory alloy is utilized, the support structure 12 can be precurved and it can retain its curvature to cause the support structure 12 to form the generally curved region 18 when the support structure 12 is moved out of a catheter shaft or sheath, while still retaining sufficient flexibility to support an ablation device utilizing the support structure 12 when the ablation device is pressed against the target tissue. Accordingly, the support structure 12 is able to sustain a large deformation at a constant temperature and when the deforming force is released, the support structure 12 is able to return to its original, undeformed shape.

The support structure 12 can be insulated in accordance with an embodiment of the invention. In particular, the support structure 12 can include a layer 20 of insulating material extending over a least a portion of an outer surface of the support structure 12. The insulating material can be comprised of an electrically non-conductive material. The electrically non-conductive material can also be thermally conductive and biocompatible in accordance with various embodiments of the disclosure. For example only and without limitation, the layer 20 of insulating material can comprise a thermally conductive, electrically insulative plastic such as the plastic sold under the trademark COOLPOLY® and generally available from Cool Options, Inc. In other embodiments of the invention, the layer 20 of insulating material can be compromised of diamond, diamond-like carbon (DLC), or polytetrafluoroethylene (PTFE), which is commonly sold by the E.I. du Pont de Nemours and Company under the trademark TEFLON®. In an embodiment of the disclosure, the layer 20 of insulating material can be provided around the entire outer perimeter of the support structure 12. However, the layer 20 of insulating material provided around the outer perimeter of the support structure 12 can vary depending on the relative requirements of the support structure 12. In an embodiment of the disclosure, the layer 20 of insulating material can be provided only along one or more portions of the length of the support structure 12. However, the amount of the layer 20 provided along the length of the support structure 12 or portion thereof can also vary depending on the relative requirements of the support structure 12.

The support structure 12 can also have sufficient strength so as to support other structural elements of the ablation device, such as the ablation electrode 14, sensing electrodes (not shown), thermal sensors (not shown), and fluid channels (not shown). For example, sensing electrodes can be used, for example, with a visualization, navigation, and mapping system. The sensing electrodes can be configured to provide a signal indicative of both a position and an orientation of at least a portion of the ablation device 10. The visualization, navigation, and/or mapping system with which the sensing electrodes can be used can comprise an electric field-based system, or sometimes referred to as an impedance-based system, such as, for example, that having the model name ENSITE NAVX™ (aka ENSITE™ Classic as well as newer versions of the ENSITE™ system, denoted as ENSITE VELOCITY™) and available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the sensing electrodes can be configured to be responsive to an electric field transmitted within the body of the patient. The sensing electrodes can be used to sense an impedance at a particular location and transmit a representative signal to an external computer or processor. In other exemplary embodiments, however, the visualization, navigation, and/or mapping system can comprise other types of systems, such as, for example and without limitation: a magnetic field- and current-based system such as the CARTO® 3 System (with current- and magnetically-driven or receptive electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS™ system or MediGuide™ technology available from Medi-Guide Ltd. of Haifa, Israel (now owned by St. Jude Medical, Inc. and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the ablation device can be configured to include field sensors (e.g., coils) responsive to a magnetic field transmitted through the body of the patient to sense the strength of the field at a particular location and transmit a representative signal to an external computer or processor. Such field sensors can comprise one or more metallic coils located on or within the ablation device in a magnetic field-based system. As noted above, a combination electric field-based and magnetic field-based system such as the CARTO® 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the ablation device can include both impedance-based sensing electrodes and one or more magnetic field-sensing coils. Commonly available fluoroscopic, computed tomography (CT), and magnetic resonance imaging (MRI)-based systems can also be used.

In some embodiments of the disclosure, the layer 20 of insulating material can include one or more first passageways (not shown). One or more thermal sensors (not shown) can be disposed within the first passageways. The first passageways can generally extend through the layer 20 along the length of the support structure 12 in accordance with an embodiment of the disclosure. The thermal sensors can be configured to measure the temperature of the ablation device 10 at one or more locations on the ablation device 10. The layer 20 of insulating material can further include one or more second passageways (not shown) that comprise fluid channels and/or ports for carrying and/or dispersing fluid such as irrigation fluid.

Figure 1A:
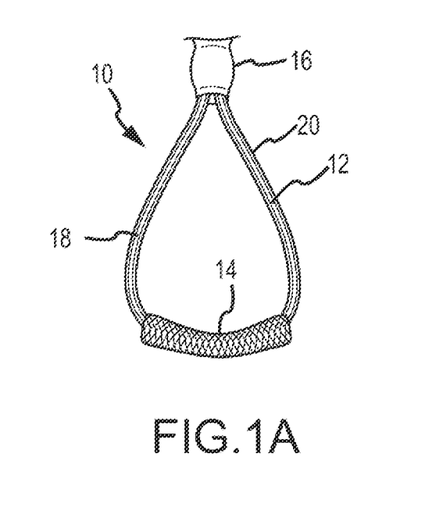
FIG. 1A is a perspective view of an ablation device under low contact pressure in accordance with a first embodiment of the disclosure.
Figure 1B:
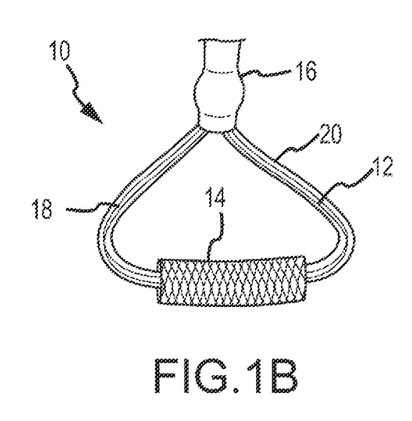
FIG. 1B is a perspective view of an ablation device under medium contact pressure in accordance with a first embodiment of the disclosure.
Figure 1C:
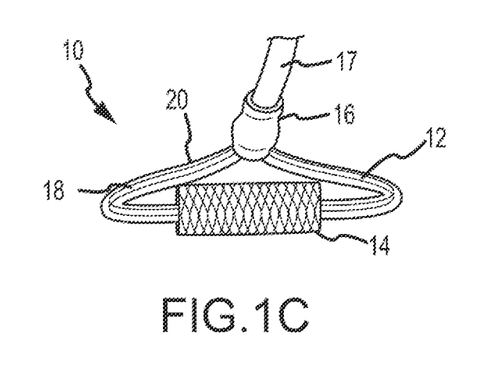
FIG. 1C is a perspective view of an ablation device under high contact pressure in accordance with a first embodiment of the disclosure.
Figure 2A:
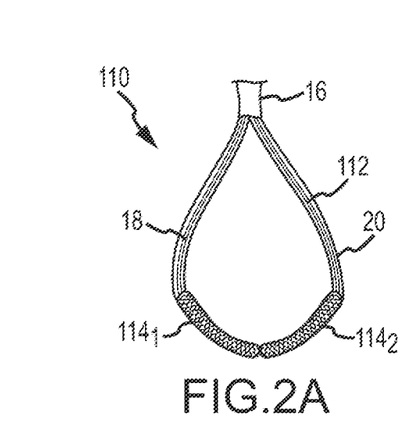
FIG. 2A is a perspective view of an ablation device under low contact pressure in accordance with a second embodiment of the disclosure.
Figure 2B:
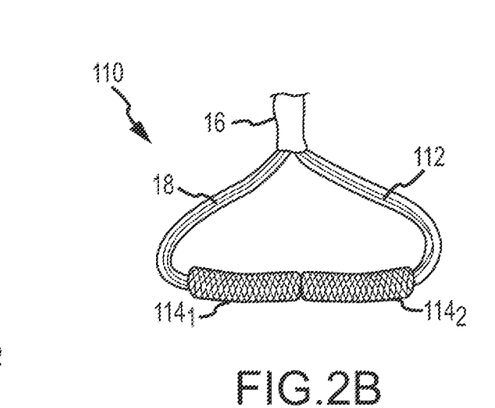
FIG. 2B is a perspective view of an ablation device under medium contact pressure in accordance with a second embodiment of the disclosure.
Figure 2C:
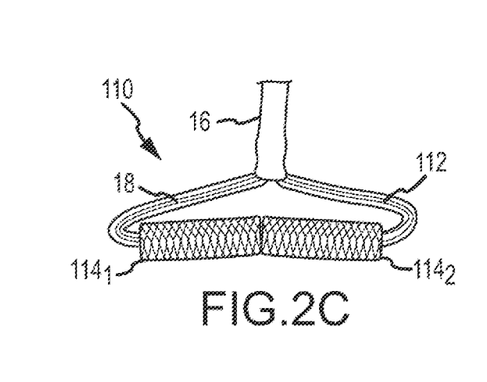
FIG. 2C is a perspective view of an ablation device under high contact pressure in accordance with a second embodiment of the disclosure.
Figure 4A:
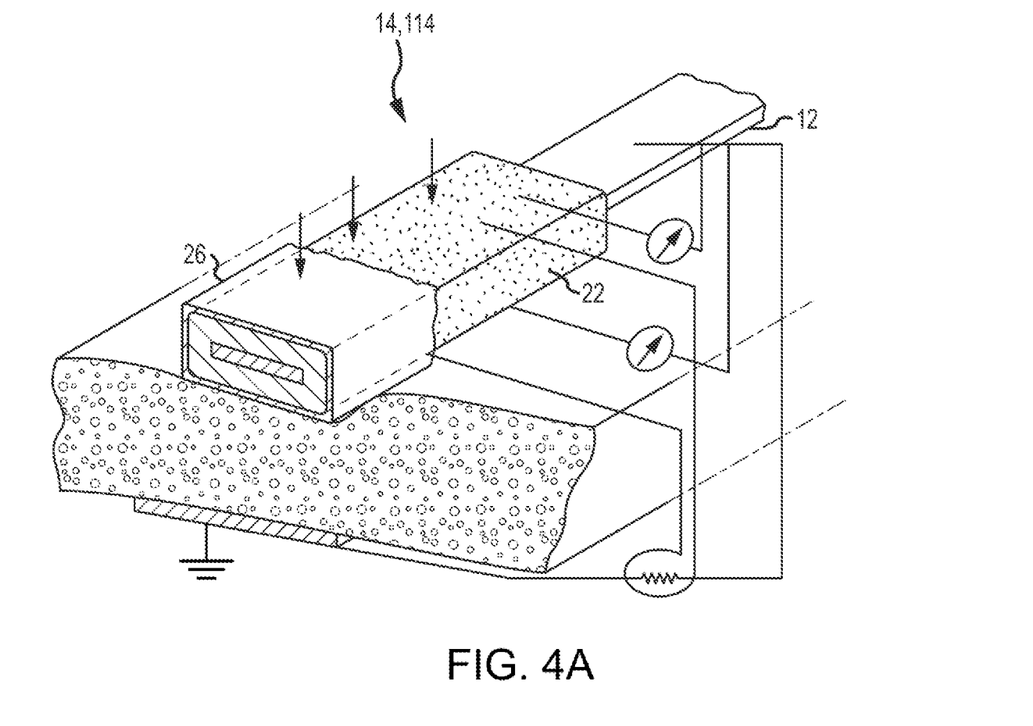
FIG. 4A is a perspective view of a portion of the ablation device of FIGS. 1-3.

Referring now to FIGS. 1A-1C and 2A-2C, the electrode 14, 114 can be disposed on the support structure 12, 112. In accordance with a first embodiment of the invention as generally illustrated in FIGS. 1A-1C, an electrode 14 may be disposed on the support structure 12. In accordance with a second embodiment of the invention as generally illustrated in FIGS. 2A-2C, a split electrode 114 may be disposed on the support structure 112. Split electrode 114 is substantially identical to electrode 14, except that split electrode 114 includes at least two separated electrode portions 114$_1$, 114$_2$ comprising split electrode 114. Referring now to FIG. 4A, the electrode 14, 114 may comprise a pressure sensitive conductive composite (PSCC) 22. When used in this application, the terms "pressure sensitive conductive composite" and/or "PSCC" means a pressure sensitive conductive composite that has unique electrical properties as follows: the electrical resistance of the PSCC varies inversely in proportion to pressure that is applied to the PSCC. An exemplary PSCC material that may be useful with the present disclosure has a high electrical resistance when not under stress (that is, in a quiescent state), and yet the same PSCC material starts to become increasingly conductive under pressure. For example and without limitation, the electrical resistance of the PSCC can fall to less than one ohm (1Ω) when under sufficient pressure corresponding to a predefined amount of pressure. When in a quiescent state, the PSCC material can have a resistance that is greater than 100,000 ohms (100,000Ω) in an embodiment of the disclosure. In another embodiment of the disclosure, when in a quiescent state, the PSCC material can have a resistance that is greater than 1M ohms (1,000,000Ω). In another embodiment of the disclosure, when in a quiescent state, the PSCC material can have a resistance that is greater than 10M ohms (1,000,000Ω). When the PSCC material has a resistance greater than 10M ohms, the PSCC material is a nonconductor in its quiescent state. The PSCC can also meet cytotoxity, hemolysis, systemic toxicity, and intracutaneous injection standards.

The PSCC 22 can comprise any number of various PSCC materials. For example, U.S. Pat. No. 6,999,821 entitled "Body implantable lead including one or more conductive polymer electrodes and methods for fabricating same" (which is incorporated by reference in its entirety as though fully set forth herein) discloses a conductor-filled polymer that can be useful in the present disclosure. For example, as disclosed therein, conductor filled polymers can include presently available materials approved for implantation in a human body such as silicone rubber with embedded metallic carbon or graphite particles or powder. Silver filled silicone rubber of the kind manufactured by NuSil Technology LLC or Specialty Silicone Products, modified so as to be approved for implantation, are of potential utility. An example is silver-coated, nickel-filled silicone rubber sold as NUSIL® R2637 and generally available from NuSil Technology LLC. The substrate for the PSCC 22 need not be silicone in accordance with other embodiments of the disclosure. For example and without limitation, it is contemplated that other insulating or weakly conductive alloys and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series, and if appropriate, at least one electroconductive agent). The conductive material can be in the form of powder, grains, fibers, or other shaped forms. The oxides can be mixtures comprising sintered powders of an oxycompound. The alloy can be conventional, or for example, titanium boride.

Other examples of PSCC materials that can be used in the present disclosure include the conductive polymers described and disclosed in U.S. Pat. No. 6,646,540 entitled "Conductive Structures;" U.S. Pat. No. 6,495,069 entitled "Polymer Composition;" and U.S. Pat. No. 6,291,568 entitled "Polymer Composition" which are each incorporated by reference in its entirety as though fully set forth herein. The materials described therein have a variable resistance of greater than $10^{12}$ ohms before any stress is applied and range to less than 1 ohm when finger pressure is applied. PSCC materials are also described and disclosed in U.S. application Ser. No. 11/647,316, now U.S. Pat. No. 7,955,326 entitled "Pressure-Sensitive Conductive Composite Electrode And Method For Ablation;" U.S. application Ser. No. 11/963,321, now United States patent application publication no. 2009/0158852 entitled "Contact Sensing Flexible Conductive Polymer Electrode;" U.S. application Ser. No. 11/647,294, now U.S. Pat. No. 7,883,508 entitled "Contact-Sensitive Pressure-Sensitive Conductive Composite Electrode and Method for Ablation;" U.S. application Ser. No. 11/647,314, now United States patent application publication no. 2008/0161786 entitled "Pressure-Sensitive Conductive Composite Contact Sensor and Method for Contact Sensing;" and U.S. application Ser. No. 11/968,044, now United States patent application publication no. 2009/0171343 entitled "Pressure-Sensitive Flexible Polymer Bipolar Electrode," which are each incorporated by reference in its entirety as though fully set forth herein.

Other examples of a suitable PSCC 22 for use in the present disclosure include quantum tunneling composites (QTC), such as those available through Peratech Ltd. of Darlington, United Kingdom. Available QTC materials include the QTC pill, the QTC substrate, and the QTC cable. The QTC materials designed by Peratech Ltd. Have variable resistance values that range from greater than 10M ohms (in the absence of stress) to less than 1 ohm when under pressure meeting a predetermined threshold value. For example and without limitation, the PSCC 22 can comprise a QTC 'pill' as generally illustrated in FIG. 4A. For example and without limitation, a QTC pill can be substantially rectangular in shape with a length and width of about a few millimeters and a thickness of about one millimeter. For example and without limitation, the length and width of a QTC pill can be about 3.6 millimeters. Although these dimensions are mentioned in detail, other dimensions for a QTC pill can be utilized in accordance with other embodiments of the disclosure. In accordance with an embodiment of the disclosure, a support structure, such as support structure 12 (see FIGS. 1A-1C) can pierce at least one QTC pill and extend through the approximate center of the QTC pill as generally illustrated in FIG. 4A. In accordance with some embodiments of the disclosure, the support structure 12 can pierce about four QTC pills and can extend through the approximate center of each of the QTC pills. Although four QTC pills are mentioned in detail, fewer or more QTC pills can be utilized in accordance with various embodiments of the disclosure.

Figure 5:
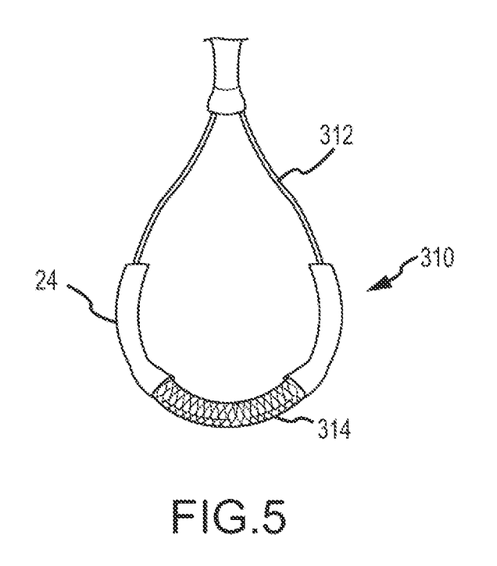
FIG. 5 is a perspective view of an ablation device in accordance with a fourth embodiment of the invention.
Figure 6:
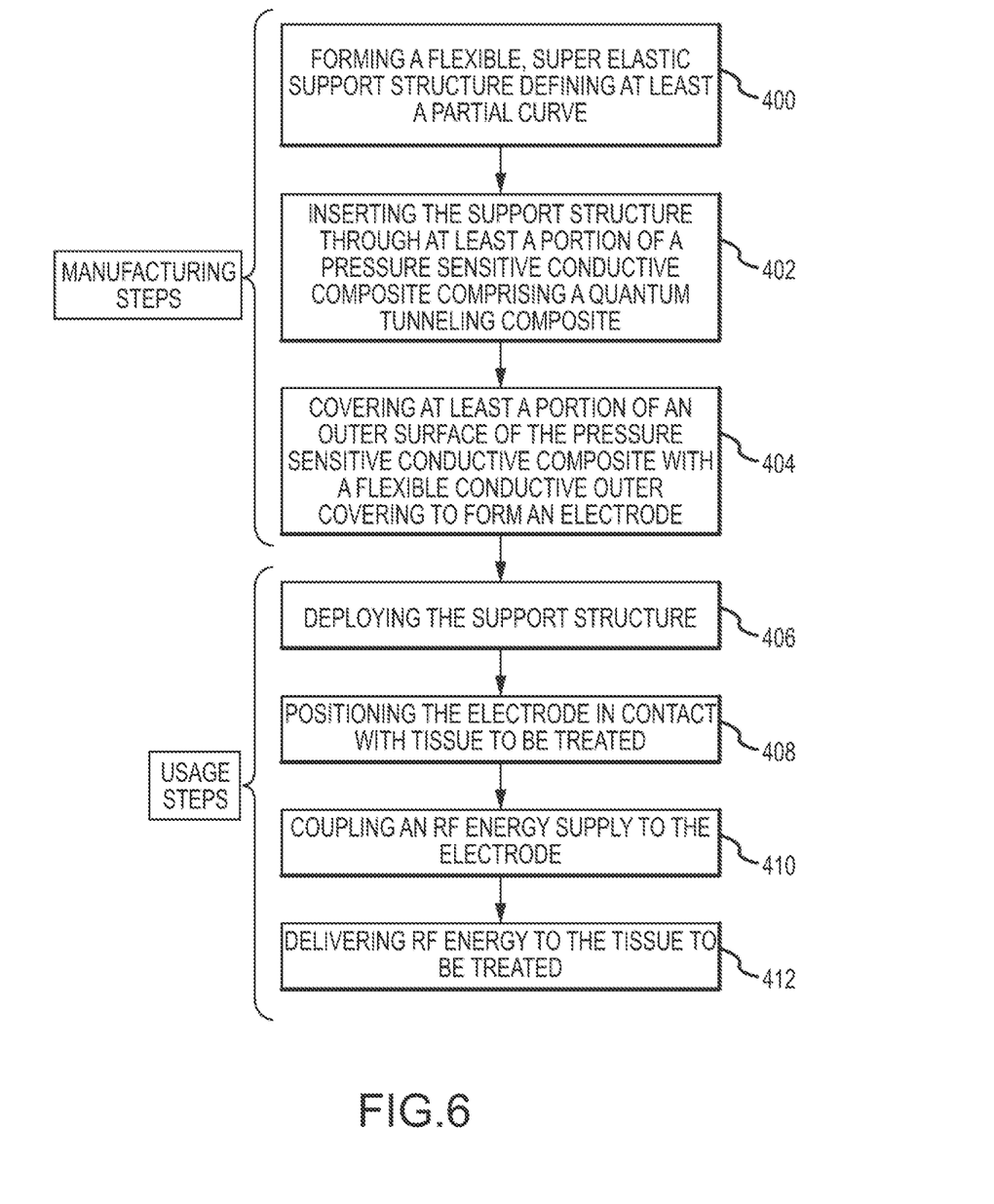
FIG. 6 is a flow chart illustrating an exemplary method of manufacturing and using an ablation device configured for creating linear lesions.

Referring now to FIG. 5, in accordance with some embodiments of the disclosure, heat shrinkable tubing 24 may extend over at least a portion of a support structure 312 of an ablation device 310, generally similar to ablation devices 10, 110 described above, but also including tubing 24 extending over at least a portion of an electrode 314. While support structure 312 may be different structurally from support structures 12, 112 (e.g., each may have a different loop length), support structure 312 may be generally similar to support structures 12, 112 and the description herein regarding support structures 12, 112 may equally apply to support structure 312. As mentioned above, the heat shrinkable tubing 24 may also extend over at least a portion of the electrode 14, 114 shown in FIGS. 1A-1C and 2A-2C, respectively. In particular, the heat shrinkable tubing may extend over at least each end of the electrode 14, 114. The use of heat shrinkable tubing 24 can help ensure that the support structure 12, 112 is mechanically connected and/or fixed to the electrode 14, 114. The heat shrinkable tubing 24 can be thin-walled in accordance with an embodiment of the disclosure. The heat shrinkable tubing 24 can comprise multiple layers in an embodiment of the disclosure. An ablation device, such as device 310, can desirably be heated to allow the heat shrinkable tubing 24 to shrink and recover its pre-expanded shape.

As a result of its unique property, materials comprising PSCC can be described as having an ability to transform from an effective insulator to a metal-like conductor when deformed by compression, twisting, or stretching. The electrical response of a PSCC can be tuned appropriately to the spectrum of pressures being applied. Its resistance range often varies from greater than 10M Ω to less than 1Ω The transition from insulator to conductor often follows a smooth and repeatable curve, with the resistance dropping monotonically to the pressure applied. Moreover, the effect is reversible in the sense that once the pressure is removed, the electrical resistance is also restored. Thus, a PSCC can be transformed from an insulator to a conductor, and back to an insulator, simply by applying an appropriate amount of pressure. PSCCs may carry large currents (e.g., up to 10 Amps) and support large voltages (e.g., 40 V and higher). A PSCC being used in connection with the present disclosure can transform from an insulator (that is, conducting little or no current) to an effective conductor simply by applying a small change in pressure to the PSCC. For example, by applying pressure with a hand, or more particularly, with a finger, a surgeon can transform the PSCC from an insulator to a conductor to permit contact sensing. Similarly, applying pressure against tissue during a surgical procedure may likewise transform the PSCC from an insulator to a conductor.

The PSCC 22 used in the present disclosure may also be chosen or customized to be of a specific pressure sensitivity such that the transformation from an insulator to a conductor occurs over a wide or narrow range of pressure. For example, highly sensitive PSCCs, which register a sharp change in resistance with a finite amount of applied pressure, may be preferred for soft contact applications such as the atrial wall. Less sensitive PSCCs, which require more pressure to register the same amount of change in resistance, may be preferred for hard contact applications such as ablation in ventricular walls.

Because a PSCC's resistance drops monotonically as pressure increases, an electrode 14 comprising PSCC 22 is able to deliver energy for ablation gradually, and then increasingly as pressure increases. Thus, the present invention permits ablation with a "soft start" and self-regulation of ablation current based on contact pressure. Because an electrode 14 comprising PSCC 22 can be used to deliver ablation with a "soft start," the electrode 14 of the present disclosure may be used in direct contact with the target tissue, thereby eliminating the physical gap that sometimes exists with other ablation electrodes. Eliminating the gap reduces the possibility of arcing, and thereby improves the safety and efficacy of ablation.

According to various embodiments, an electrode, such as electrode 14, 114 (FIGS. 1A-1C and 2A-2C), can be fabricated of a PSCC 22 (see FIG. 4A) that can differentiate between a soft and a hard push in accordance with some embodiments of the disclosure. Such a device can be used to switch, for example, an ablation electrode in response to a concentrated pressure while ignoring the general background pressure. Alternatively, such a device can "turn on" and deliver electrical energy that is already present within the device. Thus, by utilizing an electrode 14, 114 made with PSCC 22, the present disclosure permits an electrode 14, 114 for delivering electrical energy for ablation, and indeed, can be designed for self actuation to deliver the electrical energy once the applied pressure exceeds a certain threshold.

The unique properties of a PSCC permit the creation of novel and pressure-sensitive current-control devices for the direct control of electrodes for various forms of electrical energy, including RF energy. The unique properties permit the creation of novel and pressure-sensitive sensors to assess contact between the sensors and tissue that may be the subject of ablation.

When the electrode 14, 114 comprising PSCC 22 is in a relatively contact free environment (such as air, or in the flowing blood stream while inside a blood vessel or heart chamber), the PSCC 22 is an insulator. When used for an ablation application, however, the electrode 14, 114 comprising PSCC is placed against tissue. As the contact pressure increases as shown in FIGS. 1A-1C and FIGS. 2A-2C, the PSCC 22 of the electrode 14, 114 becomes conductive and permits the degree of contact to activate and/or control operation of electrode 14, 114 comprising PSCC 22. Because of the unique properties of a PSCC, only that portion of the electrode 14, 114 comprising PSCC that is in contact with the tissue becomes conductive. Those portions which are not in direct contact with the tissue, such as the region facing the blood, remain non-conductive, thereby mitigating any current leakage that may cause coagulum and thrombus formation. The resistance of an electrode 14, 114 comprising PSCC 22 changes anisotropically, based on the variation of the contact pressure on the electrode 14, 114. Thus, the contact pressure at the electrode-tissue interface is maximum at the point (or line) of normal incidence and gradually decreases along the arc of contact to zero at the edge of the contact. Because of its ability to direct RF energy to the point of contact, the electrode 14, 114 is omni-directional in use, but tissue-directional in application. The RF energy passes mostly into the tissue where appropriate tissue contact is being made and minimally into blood or other tissue. This offers significant advantages, including increased efficiency, over other ablation electrodes. The PSCC 22 of electrode 14, 114 can be configured for electrical communication with an electrical conductor (not shown), which may in turn be connected to a radiofrequency (RF) generator or RF current source.

Figure 4B:
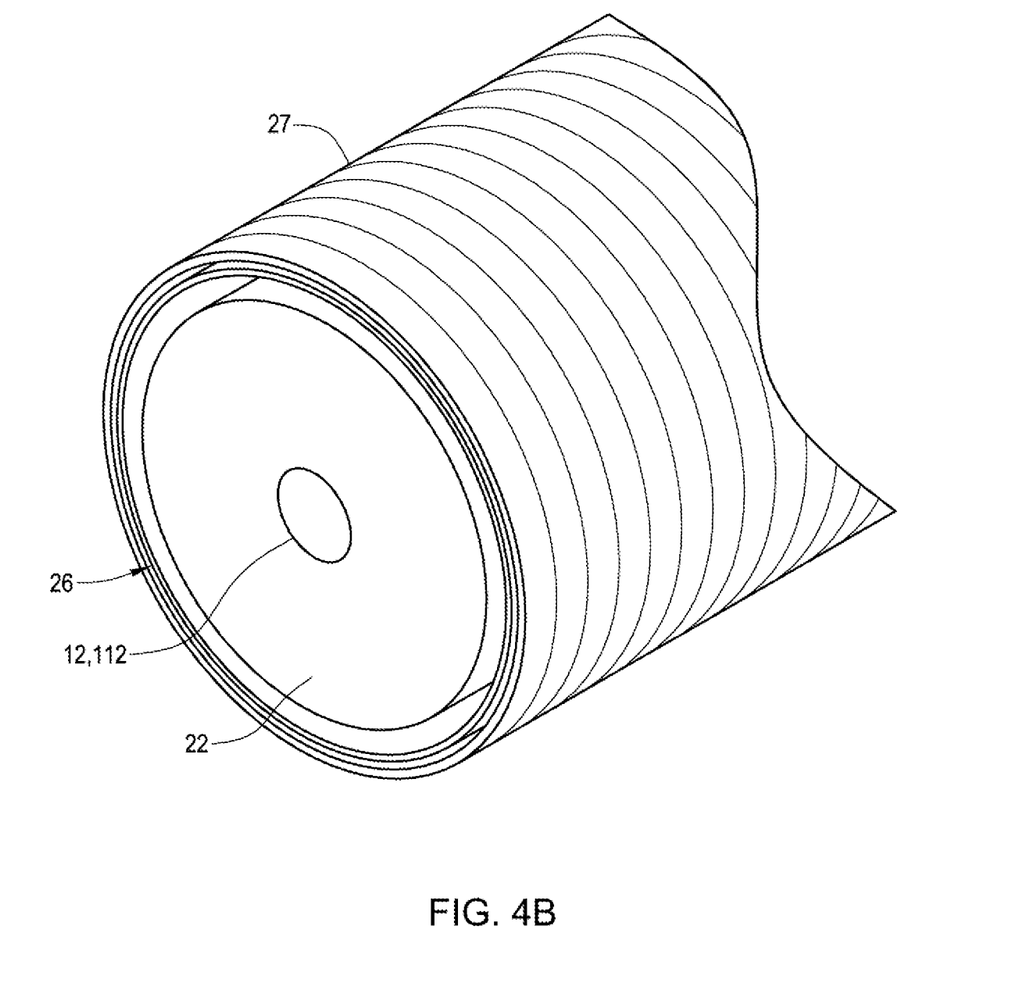
FIG. 4B is a perspective view of a portion of the ablation device of FIGS. 1-3 in accordance with another embodiment of the disclosure.

Referring back to FIG. 4A, it is contemplated that one or more electrically-conductive outer coverings 26 can be optionally utilized in accordance with the ablation devices referenced hereinabove. For example and without limitation, the outer covering 26 can be electrically conductive. In particular, the outer covering 26 can be in electrically conductive contact with the PSCC 22. The outer covering 26 can comprise a flexible wire mesh, a conductive helical coil 27, a conductive fabric, a conductive polymer layer (which can be porous or nonporous), a metal coating, and/or any other suitable form of conductive material. In the embodiment shown in FIG. 4B, the outer covering 26 comprises the conductive helical coil 27. The outer covering 26 can surround, partially or wholly, the PSCC 22. The outer covering 26 can be used to not only enhance the mechanical integrity, but to enhance the ability of the PSCC 22 to assess the tissue contact. In some embodiments of the disclosure, the outer covering 26 can be made using a biocompatible material in order to help make the ablation device 10, 110 (FIGS. 1A-1C and 2A-2C) overall biocompatible. In accordance with an embodiment of the disclosure, the outer covering 26 is flexible. Examples of flexible outer covering materials that can be used in the present disclosure include the flexible conductive polymers described and disclosed in U.S. application Ser. No. 11/963,430, now United States patent application publication no. 2009/0163916 entitled "Flexible Conductive Polymer Electrode and Method for Ablation" which is hereby incorporated by reference in its entirety as though fully set forth herein.

For example and without limitation, the outer covering 26 can comprise a conductive polymer, such as polyacetylene, polypyrrole, polyanaline, or a combination thereof. In addition, conductor-filled polymers can include presently available materials approved for implantation such as silicone rubber with embedded metallic carbon or graphite particles or powder. Silver filled silicone rubbers of the kind manufactured by NuSil Technology LLC or Specialty Silicone Products, modified so as to be approved for implantation, are of potential utility. An example is silver-coated, nickel-filled silicone rubber sold as NUSIL® R2637 and generally available from NuSil Technology LLC. The substrate for the outer covering 26 need not be silicone in accordance with other embodiments of the disclosure. For example and without limitation, it is contemplated that other insulating or weakly conductive alloys and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series, and if appropriate, at least one electroconductive agent). The conductive material can be in the form of powder, grains, fibers, or other shaped forms. The oxides can be mixtures comprising sintered powders of an oxycompound. The alloy can be conventional, or for example, titanium boride. In accordance with an embodiment of the invention, the outer covering 26 can comprise a conductive silver fabric. For example and without limitation, the outer covering 26 can comprise 3M™ Conductive Silver Fabric Tape AG-2300 generally available from 3M.

In accordance with the first and second embodiments of the invention, the ablation device 10, 110 can be configured for passive deployment as generally illustrated in FIGS. 1A-1C and FIGS. 2A-2C. In passive deployment, the support structure 12, 112 is configured to deform upon the application of pressure to the support structure. There is no direct or active control of when or how quickly the support structure 12, 112 deforms or returns to its original shape. However, in accordance with a third embodiment of the invention and referring to FIGS. 3A-3C, the ablation device 210 can be configured for active deployment. An embodiment utilizing active deployment may provide a more easy and controllable means of actively deforming and/or actively returning the support structure 112 to its original shape. The deformation of the support structure 112, and the return of the support structure 112 to its original shape, can maneuver the curved region 18 of the support structure 112 into or at a pulmonary vein or other cardiac structure and change the shape of the curved region 18 so that the electrode 114 along the curved region 18 of the support structure 112 is pressed against the walls of the target vein or other cardiac structure.

Figure 3A:
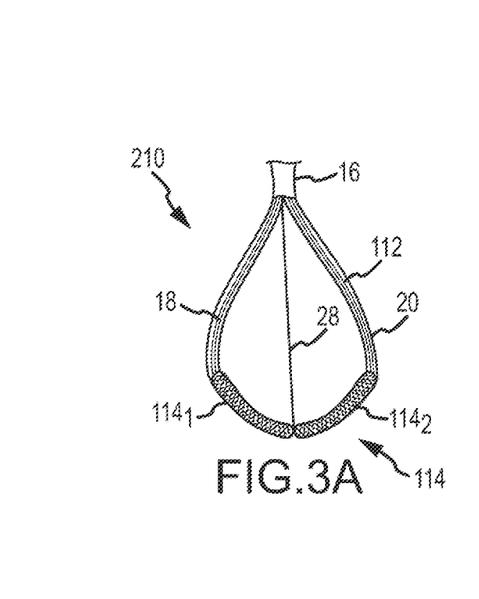
FIG. 3A is a perspective view of an ablation device under low contact pressure in accordance with a third embodiment of the disclosure.
Figure 3B:
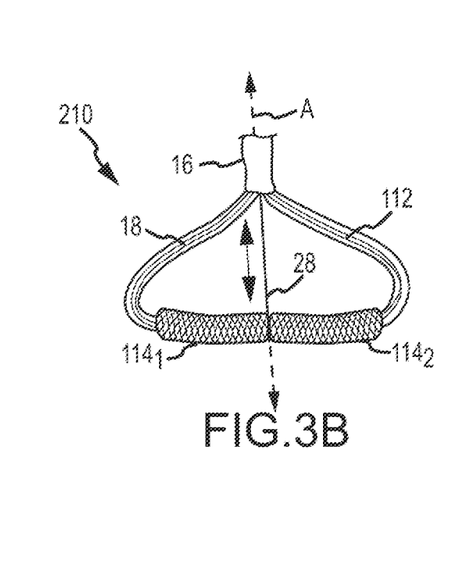
FIG. 3B is a perspective view of an ablation device under medium contact pressure in accordance with a third embodiment of the disclosure.
Figure 3C:
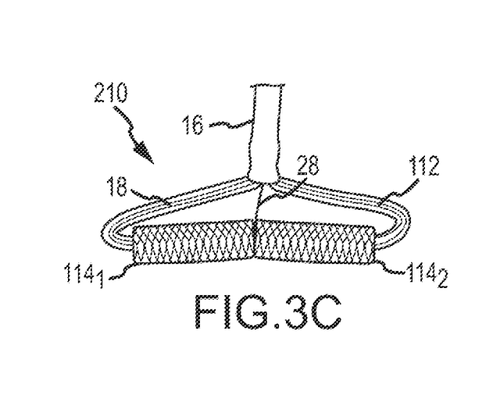
FIG. 3C is a perspective view of an ablation device under high contact pressure in accordance with a third embodiment of the disclosure.

The ablation device 210 is substantially similar to the ablation device 110 except for the addition of an active deployment member or actuator 28. In accordance with the third embodiment of the disclosure, the active deployment member 28 may comprise a moveable rod. For example and without limitation, the moveable rod may be configured for mechanical actuation. Alternatively, the moveable rod may be configured for magnetic, electrical, or any other actuation. The movable rod can be configured for movement in two opposing directions along an axis A of the straight region 16 of the ablation device 210 as best illustrated in FIG. 3B. When the moveable rod is retracted toward a proximal end of the ablation device 210, the support structure 112 can be deformed so as to form a more flat shape or configuration at a distal end of the ablation device 210 as best illustrated in FIGS. 3B-3C. When the moveable rod is extended toward the distal end of the ablation device, the support structure 112 can return to its original, more round shape having a more curved configuration at the distal end of the ablation device as best illustrated in FIG. 3A. Combinations of active and passive deployment are also possible and within the scope of the disclosure. Accordingly, the ablation device 210 can be structurally designed and configured for passive deployment, active deployment, or a combination of both. Although ablation device 210 is described and illustrated as including a split electrode 114 including at least two electrode portions $114_1$, $114_2$ comprising split electrode 114, the ablation device 210 can include an electrode 14 (with a single portion, see FIGS. 1A-1C) in accordance with other embodiments of the disclosure.

In accordance with another embodiment of the disclosure, a method of manufacturing an ablation device and using the device to create linear lesions is provided. Referring now to FIGS. 6 and 1A-1C, the manufacturing steps can include steps 400-404. Step 400 may include forming a flexible, super elastic support structure 12 defining at least a partial curve 18. The flexible, super elastic support structure 12 can comprise an insulated flat Nitinol wire in accordance with an embodiment of the disclosure. The method can further include step 402 of inserting the support structure 12 through at least a portion of a PSCC 22 comprising a quantum tunneling composite. Step 402 can include the subset of inserting the support structure 12 through a plurality of pills comprising a quantum tunneling composite. For example and without limitation, each pill can be approximately 3-4 mm in width and length and approximately 1 mm in thickness. Although these dimensions are mentioned in detail, the length, width, and thickness of each of the pills can vary in accordance with various embodiments of the disclosure. For example and without limitation, the support structure 12 can be inserted into and through approximately four pills. Electrical resistance of the quantum tunneling composite varies inversely in proportion to pressure that is applied to the quantum tunneling composite. For example and without limitation, electrical resistance of the quantum tunneling composite is configured to fall below one ohm when a predefined amount of pressure is applied to the quantum tunneling composite. In accordance with an embodiment of the disclosure, the support structure 12 can be inserted into the approximate center of each of the plurality of pills comprising a quantum tunneling composite. In accordance with an embodiment of the disclosure, a portion of the support structure 12 can be exposed at a distal end of the pills. For example and without limitation, about 20 mm of the support structure 12 can be exposed. Subsequently, about 12 mm of the layer of insulating material 20 extending over at least a portion of an outer surface of the support structure 12 can be removed from the support structure 12. The distal end of the portion of the support structure 12 without insulating material 20 and the distal end of the pills can then be aligned. For example, the support structure 12 can be pulled back, or the pills can be pushed toward the distal end of the portion of the support structure 12 without insulating material in order to align the distal ends of the support structure 12 and the pills. The method can further include the step 404 of covering at least a portion of an outer surface of the PSCC 22 with a flexible conductive outer covering 26 to form an electrode 14, 114. After the PSCC 22 is covered with a flexible conductive outer covering 26, heat shrinkable tubing 24 can be slide over at least a portion of the wrapped PSCC 22. For example and without limitation, the heat shrinkable tubing 24 can cover a portion of the wrapped PSCC 22 on a proximal end.

Still referring to FIGS. 6 and 1A-1C as well as FIGS. 2A-2C where appropriate, the usage steps to create linear lesions can include steps 406-412. Step 406 may include deploying the support structure 12. The deployment of the support structure 12 can be passive and/or active as described hereinabove. The method can further include the step 408 of positioning the electrode 14, 114 in contact with tissue to be treated. The method can further include the step 410 of coupling an RF energy supply to the electrode 14, 114. The method can further include the step 412 of delivering RF energy to the tissue to be treated.

Although four embodiments of this invention have been described above with a certain degree of particularity, those skilled in the art could make numerous alterations to the disclosed embodiments without departing from the spirit or scope of this invention. For example, although one electrode 14, 114 is generally described and illustrated, the ablation device 10, 110, 210, 310 may include two or more electrodes 14, 114 in accordance with other embodiments of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation device for creating linear lesions, the device comprising:
    a flexible support structure defining a pre-formed curve, the pre-formed curve defining a pre-formed closed loop capable of being retained in the absence of a deforming force;

an electrode disposed at a distal end of the closed loop of the flexible support structure, the electrode comprising:
   a pressure sensitive conductive composite that is configured for electrical communication with an electrical conductor, wherein electrical resistance of the pressure sensitive conductive composite varies inversely in proportion to pressure that is applied to the pressure sensitive conductive composite; and
   a flexible conductive outer covering that covers at least a portion of the pressure sensitive conductive composite; and
an active deployment member configured to controllably deform the flexible support structure;
wherein the electrode is configured to form a linear lesion when a longitudinal axis of the electrode is substantially transverse to a longitudinal axis of the ablation device; and
wherein the flexible conductive outer covering comprises a conductive helical coil.

2. The ablation device of claim 1, wherein the support structure is super elastic.

3. The ablation device of claim 1, wherein the support structure comprises a flat wire.

4. The ablation device of claim 1, wherein the support structure includes a layer of insulating material extending over at least a portion of an outer surface of the support structure.

5. The ablation device of claim 1, wherein the pressure sensitive conductive composite has an electrical resistance greater than 100,000 ohms in a quiescent state.

6. The ablation device of claim 1, wherein the pressure sensitive conductive composite has an electrical resistance greater than 1M ohms in a quiescent state.

7. The ablation device of claim 1, wherein the pressure sensitive conductive composite has an electrical resistance greater than 10M ohms in a quiescent state.

8. The ablation device of claim 1, wherein the electrical resistance of the pressure sensitive conductive composite is configured to fall below one ohm when a predefined amount of pressure is applied to the pressure sensitive conductive composite.

9. The ablation device of claim 1, wherein the pressure sensitive conductive composite comprises a quantum tunneling composite.

10. The ablation device of claim 1, wherein the flexible conductive outer covering is in electrically conductive contact with the pressure sensitive conductive composite.

11. The ablation device of claim 1, wherein the flexible conductive outer covering comprises polyacetylene, polypyrrole, polyanaline, or a combination thereof.

12. The ablation device of claim 1, wherein the flexible conductive outer covering comprises a nonconductive polymer with electrically conductive particles dispersed therein.

13. The ablation device of claim 12, wherein the nonconductive polymer comprises silicone.

14. The ablation device of claim 12, wherein the electrically conductive particles comprise gold, silver, platinum, iridium, titanium, tungsten, or a combination thereof.

15. The ablation device of claim 1, wherein the flexible conductive outer covering comprises a conductive silver fabric.

16. The ablation device of claim 1, wherein the electrode is disposed only at a distal end of the closed loop.

17. The ablation device of claim 1, wherein the active deployment member comprises a movable rod.

18. The ablation device of claim 1, wherein the active deployment member is configured to controllably deform the pre-formed closed loop.

19. The ablation device of claim 1, wherein the electrode is configured to form a linear lesion that is substantially transverse to a longitudinal axis of the active deployment member.

20. The ablation device of claim 1, wherein the active deployment member is configured for at least one of magnetic or electrical actuation.

21. An ablation device for creating linear lesions, the device comprising:
   a flexible support structure defining a pre-formed curve, the pre-formed curve defining a pre-formed shape capable of being retained in the absence of a deforming force;
   an electrode disposed on the flexible support structure, the electrode comprising:
      a pressure sensitive conductive composite that is configured for electrical communication with an electrical conductor, wherein electrical resistance of the pressure sensitive conductive composite varies inversely in proportion to pressure that is applied to the pressure sensitive conductive composite; and
      a flexible conductive outer covering that covers at least a portion of the pressure sensitive conductive composite; and
   an active deployment member configured to controllably deform the flexible support structure;
   wherein the electrode is configured to form a linear lesion when a longitudinal axis of the electrode is substantially transverse to a longitudinal axis of the ablation device;
   wherein the active deployment member is configured for at least one of magnetic or electrical actuation; and
   wherein the flexible conductive outer covering comprises a conductive helical coil.

22. The ablation device of claim 21, wherein the pre-formed shape comprises a closed loop; and wherein the electrode is disposed at a distal end of the closed loop.

23. The ablation device of claim 21, wherein the pre-formed shape comprises a closed loop, and wherein the electrode is disposed only at a distal end of the closed loop.

24. The ablation device of claim 21, wherein the active deployment member comprises a movable rod.

25. The ablation device of claim 21, wherein the active deployment member is configured to controllably deform the pre-formed shape.

26. The ablation device of claim 21, wherein the electrode is configured to form a linear lesion that is substantially transverse to a longitudinal axis of the active deployment member.

27. An ablation device for creating linear lesions, the device comprising:
   a flexible support structure defining a pre-formed curve, the pre-formed curve defining a pre-formed closed loop capable of being retained in the absence of a deforming force; and
   an electrode disposed at a distal end of the closed loop of the flexible support structure, the electrode comprising:
      a pressure sensitive conductive composite that is configured for electrical communication with an electrical conductor, wherein electrical resistance of the pressure sensitive conductive composite varies inversely in proportion to pressure that is applied to the pressure sensitive conductive composite; and a flexible conductive outer covering that covers at least a portion of the pressure sensitive conductive composite;

wherein the electrode is configured to form a linear lesion when a longitudinal axis of the electrode is substantially transverse to a longitudinal axis of the ablation device; and wherein the flexible conductive outer covering comprises a conductive helical coil.

* * * * *